United States Patent [19]

Gunther

[11] 4,069,153

[45] Jan. 17, 1978

[54] METHOD OF DESTROYING PYROGENS

[75] Inventor: Donald A. Gunther, Erie, Pa.

[73] Assignee: American Sterilizer Company, Erie, Pa.

[21] Appl. No.: 738,925

[22] Filed: Nov. 4, 1976

Related U.S. Application Data

[63] Continuation of Ser. No. 625,821, Oct. 28, 1975, abandoned.

[51] Int. Cl.² ............................................. C02B 3/00
[52] U.S. Cl. ...................................... 210/64; 210/192; 21/54 R; 21/DIG. 2
[58] Field of Search ....................... 210/64, 192, 63 Z; 21/102 R, 54 R, DIG. 2

[56] References Cited

U.S. PATENT DOCUMENTS

| | | | |
|---|---|---|---|
| 3,336,099 | 8/1967 | Czulak et al. ...................... | 21/102 R |
| 3,672,823 | 6/1972 | Boucher ............................. | 21/102 R |
| 3,700,406 | 10/1972 | Landry ............................... | 21/102 R |
| 3,791,790 | 2/1974 | Wyndham et al. .................... | 210/64 |
| 3,837,800 | 9/1974 | Wood .................................. | 210/64 |

FOREIGN PATENT DOCUMENTS 674,555   11/1963   Canada .............................. 21/102 R Primary Examiner—Charles N. Hart
Assistant Examiner—Benoit Castel
Attorney, Agent, or Firm—Charles L. Lovercheck

[57] ABSTRACT

A method of providing a continuous available supply of physiologically safe water for use in fluid therapy by providing a sub-micron filter to remove bacteria at the source, and by continuously treating the water with ultraviolet light at a frequency range and dosage sufficient to destroy substantially all pyrogenicity and organisms, such as viruses, that are not retained by the filter.

2 Claims, 6 Drawing Figures

U.S. Patent  Jan. 17, 1978  4,069,153
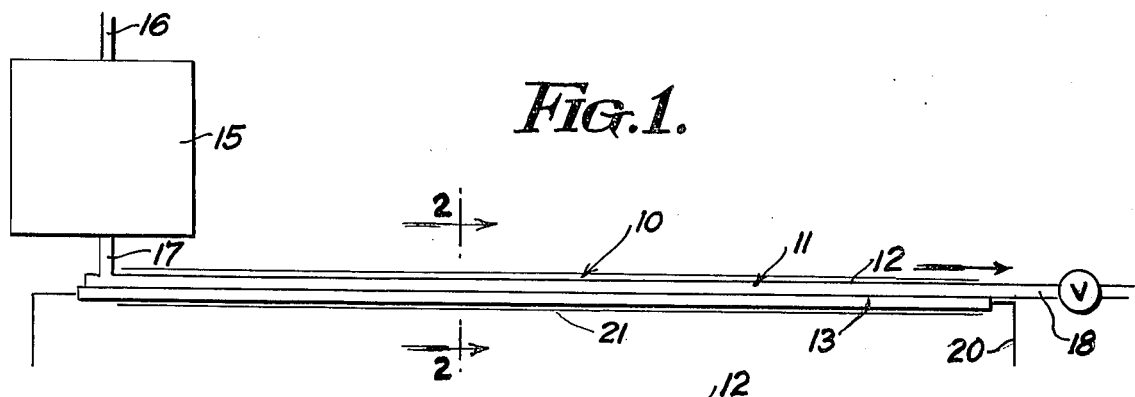
FIG.1.
FIG.2.
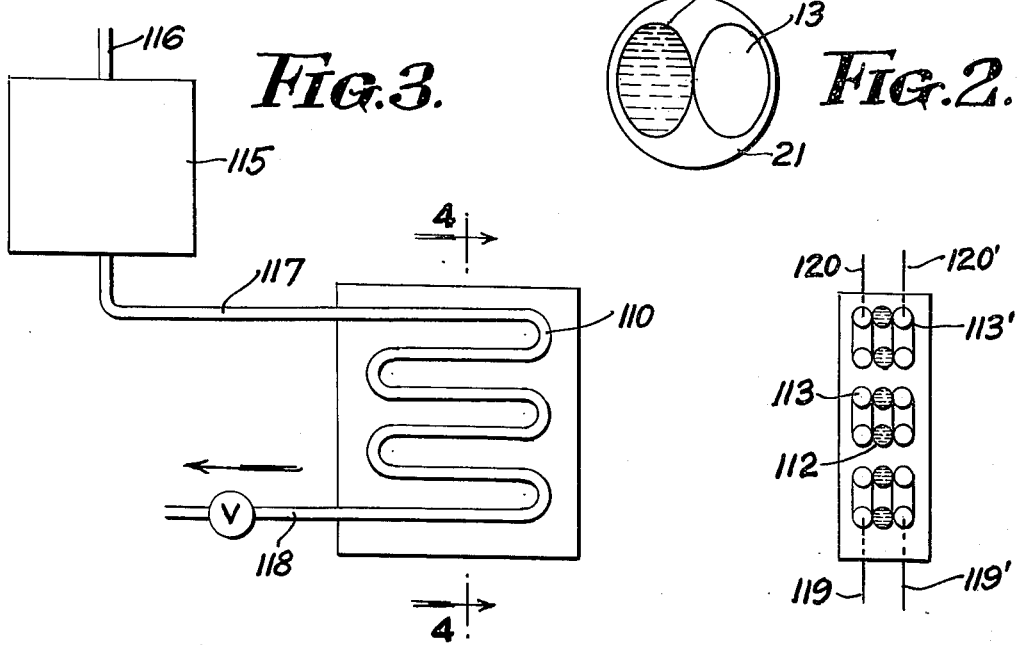
FIG.3.
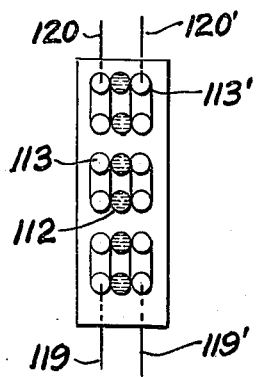
FIG.4.
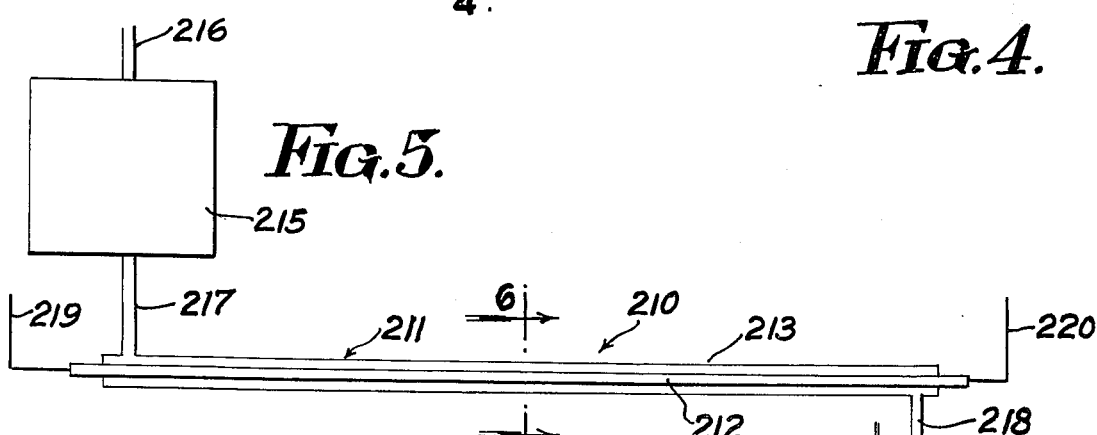
FIG.5.
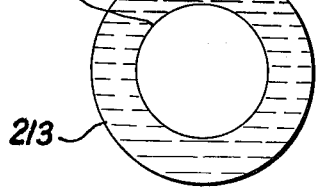
FIG.6.

METHOD OF DESTROYING PYROGENS

This is a division continuation of application Ser. No. 625,821 filed Oct. 28, 1975 now abandoned.

GENERAL DESCRIPTION OF INVENTION

Pyrogens, as used in my disclosure, refer to microbial endotoxins capable of producing fever in mammals. The "pyrogens" are metabolic products of certain microorganisms such as *E. coli, S. enteritidis, Pseudomonas aeruginosa, B. cereus, S. faecalis, Aspergillus niger*, and many others; they are chemically classified as lipopolysaccharides.

I have demonstrated the effectiveness of my system by preparing pyrogenic solutions of distilled water and subjecting them to the system and dosage disclosed. The solutions were pyrogenic before treatment and non-pyrogenic after treatment as determined by the standard U.S.P. Pyrogen Test. The various solutions tested were: (a) the microorganism E. coli added to distilled water to produce a population of $10^7$ per liter; (b) Difco lipoplysaccharide 3880 (E. coli endotoxin) added to distilled water to make a concentration of 2 micrograms per ml; (c) Difco lipopolysaccharide 3126 (S. entertidis endotoxin) added to distilled water to make a concentration of 2 micrograms per ml.

REFERENCE TO PRIOR ART

U.S. Pat. No. 3,672,823 issued to Boucher on June 27, 1972 and U.S. Pat. No. 3,440,157 issued to Gunther on Apr. 22, 1969 in Class 204, Subclass 152.

OBJECTS OF THE INVENTION

It is an object of the invention to provide an improved method of providing physiological water.

Another object of the invention is to provide an improved method for destroying pyrogens.

GENERAL DESCRIPTION OF DRAWINGS

FIG. 1 is a schematic view of an irradiator according to the invention.

FIG. 2 is a cross sectional view taken on line 2—2 of FIG. 1.

FIG. 3 is a top view of another embodiment of the irradiator.

FIG. 4 is a cross sectional view taken on line 4—4 of FIG. 3.

FIG. 5 is a schematic sectional view of another embodiment of the invention.

FIG. 6 is a cross sectional view taken on line 6—6 of FIG. 5.

DETAILED DESCRIPTION OF INVENTION

A method is disclosed for providing a continuously available supply of physiologically safe water for use in fluid therapy (as opposed to flasking). Present technique demands flasked distilled water or solutions prepared therefrom; a continuously available supply is precluded because of problems associated with achieving and maintaining sterility. The simple expedient of submicron filtration does not assure this condition and, in addition, does not provide for asepsis at the drawoff point (spigot); safeguarding against pyrogenicity is likewise not provided for.

Given a supply of suitable water, the disclosed system provides a totally safe system utilizing submicron filtration to remove bacteria, utilizes an intense source of high energy ultraviolet light in a specially designed flow cell to destroy pyrogenicity and organisms such as viruses, that are not retained by the filter. Asepsis of the drawoff point is maintained by ultraviolet radiation, enhanced by ozone produced by the ultraviolet source.

Ultraviolet sources of appropriate energy and intensity are known to be available and are effective, since the noxious agents absorb this energy and are internally destroyed or inactivated; in addition, the high energy state produced in the water by its absorbtion and peroxide formation enhance inactivation.

This invention deals with the short wave ultraviolet range (1800–3000A) which is common to patents and apparatus for disinfecting or "sterilizing" potable water, because mercury arcs emit in this range.

The ultraviolet radiating sources used for disinfecting potable water generally use a dosage of 25,000 to 35,000 microwatt-seconds/$cm^2$ at 2537A; this is approximately twice the dosage recommended in Public Health Policy 4-1-66. This dosage, 16,000 microwatt-seconds/$cm^2$, is considered adequate to inactivate the common infectious forms of microbial life.

It is well known to those skilled in the art that all radiation (photons) is not absorbed by target molecules, and all absorbed radiation (photons) do not result in chemical change. While the low dosages (25,000 to 35,000 microwatt-seconds/$cm^2$ used to disinfect potable water are sufficient to inactivate common infectious microorganisms present in this medium, they are not adequate to destroy all forms of microbial life; obviously then, they would not be sufficient to assure chemical change in all molecules present. My irradiator uses a dosage far in excess of that used to disinfect potable water; whereas, disinfecting dosages are in the order of 25,000–35,000 microwatt-seconds/$cm^2$. I use a dosage in the order of 200,000 (100,000–300,000) microwatt-seconds/$cm^2$/per square centimeter of outside area of said flow path to provide a sufficient number of photons so that all pyrogen molecules are struck by sufficient radiation to chemically alter all the molecules present.

Additionally, much of the equipment used for disinfecting potable water use radiating sources that are comprised of a glass sheath that does not transmit below 2,000A; therefore, the 1849A line is not transmitted through the source sheath and thus does not irradiate the target at this wave length. My irradiator uses a special quartz sheath which does transmit the 1849A line; this is the well known ozone-producing wave length wherein oxygen is converted to ozone (a strong oxidizer). The oxygen dissolved in the water is thus converted to ozone which may enhance pyrogen destruction (pyrogens are known to be destroyed by strong oxidizing agents). Furthermore, the 1849A line can disassociately $H_2O$ to H E and OH, which produces reactive chemically excited states. These conditions can provide a synergistic, or at least additive effect, with the radiation per se, on the molecular alteration of pyrogens.

It is common practice in irradiator design for disinfecting potable water to employ a contrivance such as a baffle to cause turbulence or directional change of the flowing water. The intent of this is to bring all the liquid within a short distance of the radiating source at some time during its passage through the irradiation apparatus; this is necessary because of the relatively large distance commonly used from the source surface and the outermost surface of the water to be irradiated. This distance is commonly 1–3inches, since ultra-violet radiation is rapidly attenuated as it passes through water, the intensity near the source is greater than at the outermost surface. Therefore, to provide "uniform" dosage of all the fluid, the water at this outermost surface must have a directional change so that it approaches the source surface at some time during passage through the irradiation apparatus; this is obviously a random, haphazard process.

In my irradiator, the maximum distance from light source 11, FIG. 1 for the radiation to penetrate is approximately 5 mm. Ideally, the irradiator consists of double bore quartz tubing, one bore containing the radiating source and the other bore containing the water or solution to be irradiated — the entire configuration is aluminized so that the total radiation is reflected toward, and passes through, the separating wall of the double bore tubing, irradiating the water, continually reflecting the nonabsorbed radiation back through the water, thus utilizing the total emitted radiation. A somwhat less efficient, but also effective irradiator is a sandwich type wherein the water to be irradiated is passed through a grid-shaped quartz tubing which is sandwiched between two quartz radiating sources of the same configuration, with the entire assembly confined in a reflective housing. The radiation from the sources on each side of the quartz tubing containing the water passes through the quartz tubing from each side, irradiates the water and continually reflects the nonabsorbed radiation back through the quartz tubing containing the water.

DETAILED DESCRIPTION OF DRAWINGS

Now, with more particular reference to the drawings, the irradiator 10 shown in FIG. 1 has a double barrel tube 11, having a bottom tube 12 and a top tube 13 intregally connected together. The tubes will be made of quartz or other transparent material having similar properties of wave transmission. The tube 12 is connected in series with the microbiocidal filter 15 which has a water inlet 16 and a water outlet 17, and tube 12 is connected with the outlet tube 18 for water to flow therefrom. The tube 13 is a mercury vapor lamp tube having electrical terminal 19 and 20. A suitable spigot V will be connected to the tube 18. A reflector 21 is disposed around the tubes 12 and 13.

In the embodiment of the invention shown in FIG. 3, and FIG. 4, the irradiator indicated generally at 110, is made up of three quartz tubes, 112, 113' and 113. Tube 112 is a water conducting tube made of quartz and connected to a filter 115 through pipe 117. Source water comes from line 116 and is discharged through line 118 and valve V. The tubes 113 and 113' are mercury lamp tubes. The tubes are supported in contact with each other and the outside periphery of the tube 112 is less than 6 millimeters from the light sources 113 and 113'. In like manner, the minor dimension of the tubes in FIG. 2 is less than 6 millimeters.

In the embodiment of the invention shown in FIGS. 5 and 6, I show an irradiator 210. Outer tube 213 is connected to the water line 217 and to the microbiocidal filter 215 and has a water inlet pipe 216 connected in series therewith. The water flows through the pipe 213 from line 217 and out the line 218.

The inner tube 212 is a lamp tube supported concentric to the outer tube 213 and has the electrical terminal 219 and 220 connected thereto. All of the tubes in each of the embodiments are made of quartz or another suitable ultra-violet passing material.

The spacing between the outside periphery of tube 212 and the inner periphery of tube 213 is less than 6 millimeters. That is, the inside periphery of tube 213 is 12 millimeters greater than the outside periphery of tube 212. Therefore, if a lamp tube 212 of 1-inch is used, the inside diameter of tube 213 would be 1.475 inches.

The foregoing specification sets forth the invention in its preferred practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A method of providing a continuous flow of physiologically safe water comprising,
   providing a continuous flow of water containing lipopolysaccharides known as pyrogens,
   treating said water containing said lipopolysaccharides with ultra-violet light of a wave length and dosage sufficient to chemically alter substantially all pyrogens in said water to destroy substantially all pyrogenicity of said water,
   said ultra-violet light being of a wave length of 1800A to 2000A at a dosage in the order of 100,000 to 300,000 microwatt-seconds per square centimeter of area of said flow path,
   with all said water flowing within 6 millimeters of said light,
   thereby converting a substantial amount of oxygen dissolved in said water to ozone, and
   whereby said pyrogen destruction is enhanced and substantially all pyrogenicity of said water is destroyed and said water is safe for physiological use.

2. The method of treating water recited in claim 1 wherein said water contains filterable bacteria and is filtered through a bacteria-retentive filter prior to treatment with said ultra-violet light.

* * * * *